United States Patent
Kim et al.

(10) Patent No.: US 10,814,022 B2
(45) Date of Patent: Oct. 27, 2020

(54) OXAMIDE NANOGEL, A PREPARATION METHOD OF THE SAME, AND USE THEREOF

(71) Applicant: KOREA INSTITUTE OF SCIENCE AND TECHNOLOGY, Seoul (KR)

(72) Inventors: Sehoon Kim, Seoul (KR); Chang-Keun Lim, Buffalo, NY (US); Jeong yun Heo, Seoul (KR); Keunsoo Jeong, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 19 days.

(21) Appl. No.: 15/581,295

(22) Filed: Apr. 28, 2017

(65) Prior Publication Data

US 2018/0064832 A1    Mar. 8, 2018

(30) Foreign Application Priority Data

Sep. 8, 2016    (KR) .................. 10-2016-0115883

(51) Int. Cl.
| | | |
|---|---|---|
| *A61K 49/22* | (2006.01) | |
| *A61K 49/00* | (2006.01) | |
| *G01N 21/64* | (2006.01) | |
| *A61K 47/34* | (2017.01) | |

(52) U.S. Cl.
CPC ............ *A61K 49/226* (2013.01); *A61K 47/34* (2013.01); *G01N 21/64* (2013.01)

(58) Field of Classification Search
None
See application file for complete search history.

(56) References Cited

U.S. PATENT DOCUMENTS

| | | | |
|---|---|---|---|
| 5,075,502 A | 12/1991 | Kneller et al. | |
| 5,505,952 A * | 4/1996 | Jiang .................. | A61L 15/26 424/423 |
| 5,611,344 A * | 3/1997 | Bernstein ............... | A61B 8/481 600/458 |
| 6,333,051 B1 * | 12/2001 | Kabanov ................ | A61K 47/34 424/484 |
| 2001/0056301 A1 * | 12/2001 | Goupil ............. | A61B 17/12022 623/11.11 |
| 2002/0123609 A1 | 9/2002 | Frechet et al. | |
| 2007/0237821 A1 * | 10/2007 | Leon .................. | A61K 49/0032 424/484 |
| 2012/0071593 A1 | 3/2012 | Andre et al. | |

FOREIGN PATENT DOCUMENTS

| | | |
|---|---|---|
| JP | 2012530163 A | 11/2012 |
| KR | 10-2014-0096821 A | 8/2014 |

OTHER PUBLICATIONS

Akers, Walter J., et al. "Noninvasive photoacoustic and fluorescence sentinel lymph node identification using dye-loaded perfluorocarbon nanoparticles." ACS nano 5.1 (2010): 173-182. (Year: 2010).*
Hamdine, Mélina, Marie-Claude Heuzey, and André Bégin. "Effect of organic and inorganic acids on concentrated chitosan solutions and gels." International Journal of Biological Macromolecules 37.3 (2005): 134-142. (Year: 2005).*
Kato, Kazuaki, and Hans-Jörg Schneider. "Cooperativity and selectivity in chemomechanical polyethylenimine gels."Langmuir;23.21 (2007): 10741-10745. (Year: 2007).*
Mohamed NA, Fahmy MM. Synthesis and antimicrobial activity of some novel cross-linked chitosan hydrogels. International journal of molecular sciences. Sep. 2012;13(9):11194-209. (Year: 2012).*

\* cited by examiner

*Primary Examiner* — Nissa M Westerberg
(74) *Attorney, Agent, or Firm* — Goldilocks Zone IP Law

(57) ABSTRACT

The present invention relates to a nanogel comprising a polyamine-based polymer cross-linked by oxamide bonds, a preparation method of the nanogel, a contrast agent for ultrasound imaging comprising the nanogel, a composition for ultrasound diagnosis of inflammatory diseases comprising the contrast agent, a preparation method of the contrast agent, and a method for providing information for diagnosis of inflammatory diseases using the composition for ultrasound diagnosis.

9 Claims, 8 Drawing Sheets

(i) 1509:N-H bending vibration(Oxamide)
(ii) 1666:C=O stretching vibration(Oxamide)
(iii) 1734:C=O stretching vibration(Oxamide)

OXAMIDE NANOGEL, A PREPARATION METHOD OF THE SAME, AND USE THEREOF

CROSS-REFERENCE TO RELATED APPLICATION

This application claims priority to Korean Patent Application No. 10-2016-0115883, filed on Sep. 8, 2016, and all the benefits accruing therefrom under 35 U.S.C. § 119, the contents of which in its entirety are herein incorporated by reference.

BACKGROUND OF THE INVENTION

(1) Field of the Invention

The present invention relates to a nanogel comprising a polyamine-based polymer cross-linked by oxamide bonds, a preparation method of the nanogel, a contrast agent for ultrasound imaging comprising the nanogel, a composition for ultrasound diagnosis of inflammatory diseases comprising the contrast agent, a preparation method of the contrast agent, and a method for providing information for diagnosis of inflammatory diseases using the composition for ultrasound diagnosis.

(2) Description of Related Art

Ultrasound imaging refers to imaging in which, after high frequency sound waves which are not heard by our ears are transmitted from a surface of a human body to inside the human body, the sound waves reflected inside are collected and visualized. Because ultrasound examination (ultrasonography or sonography) obtains ultrasound images in real time, not only the structure of an organ but also the movement thereof can be observed, and blood flow inside blood vessels can be measured as well. It is a very easy and convenient imaging method to diagnose a patient's disease or to judge the progress of a treatment thereof because it does not use radiation harmful to the human body and can quickly perform tests without pain.

Ultrasound examination is a test which detects a lesion in a patient's body while viewing 2D images in real time in a form of which the body is cut into thin cross sections, and recently, ultrasound technology has been developed so that 3D ultrasonography which shows organs or fetuses inside the body in 3 dimensions is widely performed, and 4D ultrasonography which further expresses the motion of 3D images is also used.

Such ultrasound examination can be used to examine upper abdominal organs such as liver, gallbladder, pancreas, spleen, kidney, etc., pelvic organs such as bladder, uterus, ovary, prostate, etc., and various other organs such as thyroid, breast, scrotum, musculoskeletal system, heart, etc. In general, the reason for performing ultrasound examination is to find the cause when there is pain or inflammation, and it can be used to diagnose a tumor at an initial stage in patients without symptoms.

Ultrasound examination is non-invasive and can be easily applied to a wide range, the cost is inexpensive as compared with other imaging examinations such as CT and MRI, etc., and there is an advantage in that it is harmless because it does not use radiation harmful to the human body so that there is no danger in repeated examination. However, it is not easy to read obtained ultrasound images, and unlike CT and MRI, as it is necessary to make a judgment in real time, it is very dependent on the examiner.

Therefore, in order to utilize such ultrasound imaging for diagnosis of diseases, dependency on the examiner can be reduced by facilitating reading, and in order to improve the accuracy and reliability of examinations, a contrast agent can be used as a substance which generates bubbles to confirm a lesion more clearly, based on the fact that ultrasound waves cannot penetrate through an air layer.

As such, the present inventors have made diligent research efforts to find contrast agents for ultrasound imaging for use in diagnosis of inflammatory diseases which generate hydrogen peroxide, and as a result, when a nanogel comprising a polyamine-based polymer cross-linked by oxamide bonds was used by mixing with perfluorohexane, which is a chemical species having an excellent gas-capturing ability, not only did it generate $CO_2$ at inflammatory lesions, but it was also capable of capturing the generated $CO_2$, which is advantageous for signal enhancement of ultrasound imaging, and therefore the present inventors completed the present invention by confirming that it is useful for diagnosis of inflammatory diseases including cancer.

SUMMARY OF THE INVENTION

(1) Technical Problem

An object of the present invention is to provide a nanogel comprising a polyamine-based polymer cross-linked by oxamide bonds.

Another object of the present invention is to provide a method for preparing the nanogel comprising the polyamine-based polymer cross-linked by oxamide bonds, wherein the method comprises: a first step of preparing a reverse micelle dispersion by stirring a polymer solution, wherein the polyamine-based polymer and a nonionic surfactant are dissolved in an organic solvent; and a second step of adding an oxalyl halide to the reverse micelle dispersion to form the nanogel by the oxamide bonds.

Still another object of the present invention is to provide a contrast agent for ultrasound imaging, comprising the nanogel comprising the polyamine-based polymer cross-linked by the oxamide bonds; a perfluorinated compound; and a nonionic polymeric surfactant.

Still another object of the present invention is to provide a composition for ultrasound diagnosis of inflammatory diseases, comprising the contrast agent as an active ingredient.

Still another object of the present invention is to provide a method for preparing a contrast agent for ultrasound imaging, comprising ultrasonically dispersing an aqueous solution dissolving the nanogel comprising the polyamine-based polymer cross-linked by the oxamide bonds; a perfluorinated compound; and a nonionic polymeric surfactant.

Still another object of the present invention is to provide a method for providing information for diagnosis of inflammatory diseases, comprising a first step of taking an ultrasound image of a subject to which the composition for ultrasound diagnosis was administered; and a second step of reading the ultrasound image to make a judgment that an inflammatory disease has occurred at a site where an increased signal is detected as compared to other normal tissues.

(2) Technical Solution

A first aspect of the present invention provides a nanogel comprising a polyamine-based polymer cross-linked by oxamide bonds.

A second aspect of the present invention provides a method for preparing the nanogel comprising the polyamine-based polymer cross-linked by oxamide bonds, wherein the method comprises: a first step of preparing a reverse micelle dispersion by stirring a polymer solution, wherein the polyamine-based polymer and a nonionic surfactant are dissolved in an organic solvent; and a second step of adding an oxalyl halide to the reverse micelle dispersion to form the nanogel by oxamide bonds.

A third aspect of the present invention provides a contrast agent for ultrasound imaging, comprising the nanogel comprising the polyamine-based polymer cross-linked by oxamide bonds; a perfluorinated compound; and a nonionic polymeric surfactant.

A fourth aspect of the present invention provides a composition for ultrasound diagnosis of inflammatory diseases, comprising the contrast agent for ultrasound imaging as an active ingredient.

A fifth aspect of the present invention provides a method for preparing the contrast agent for ultrasound imaging, comprising ultrasonically dispersing an aqueous solution dissolving the nanogel comprising the polyamine-based polymer cross-linked by the oxamide bonds; a perfluorinated compound; and a nonionic polymeric surfactant.

A sixth aspect of the present invention provides a method for providing information for diagnosis of inflammatory diseases, comprising a first step of taking an ultrasound image of a subject to which the composition for ultrasound diagnosis was administered; and a second step of reading the ultrasound image to make a judgment that an inflammatory disease has occurred at a site where an increased signal is detected as compared to other normal tissues.

Hereinbelow, the present invention will be described in more detail.

A representative example of a substance known in the art to react with hydrogen peroxide to generate $CO_2$ is a compound comprising oxalate bonds (R—O—(C=O)—(C=O)—O—R'). However, since a reaction in which $CO_2$ is generated by the hydrogen peroxide acting on oxalate bonds occurs too fast, it is difficult to capture the generated $CO_2$, such that the efficiency may be low if used as a contrast agent for ultrasound imaging. Accordingly, the present inventors have discovered that by using a substance comprising oxamide bonds having lower reactivity than oxalate bonds, the $CO_2$ generation rate can be controlled, and the generated $CO_2$ can be easily captured so that it is possible to use the substance as a contrast agent for ultrasound imaging. Furthermore, after making a polyamine-based polymer comprising many amine groups into a reverse micelle dispersion and reacting with an oxalyl halide, it can be provided in the form of a nanogel having a nanometer-scale diameter comprising oxamide bonds, and it is possible to provide a contrast agent comprising the same in the form of particles having a size of several tens to several hundreds of nanometers to facilitate the administration thereof. As described above, upon administration to an inflammatory lesion, the contrast agent generates $CO_2$ at a rate controlled by the reaction of oxamide bonds comprised therein and hydrogen peroxide generated in the lesion, and can thereby form bubbles in which micro-sized $CO_2$ gas is captured, and in particular, it was confirmed that by further comprising perfluorohexane with an excellent gas-capturing ability, it was possible to support $CO_2$ at a higher density and thereby make more accurate diagnoses of lesions of inflammatory diseases.

The present invention provides the nanogel comprising the polyamine-based polymer cross-linked by oxamide bonds.

For example, the polyamine-based polymer may be a linear or branched poly($C_{1-4}$ alkylene)imine. The polyamine-based polymer may be branched polyethylenimine (bPEI), but is not limited thereto. For example, the oxamide bonds may be formed at a ratio of 10 mol % to 50 mol % relative to the total number of amine groups. When the oxamide bonds are comprised at a ratio outside the range, that is, less than 10 mol % or more than 50 mol % relative to the total number of amine groups, formation of stable nanogels may not be possible.

The nanogel according to the present invention can be prepared by a method comprising: a first step of preparing a reverse micelle dispersion by stirring a polymer solution, wherein a polyamine-based polymer and a nonionic surfactant are dissolved in an organic solvent; and a second step of adding an oxalyl halide to the reverse micelle dispersion to form the nanogel by oxamide bonds.

For example, the first step may be performed by stirring at a rate of 1,000 rpm to 3,000 rpm for 15 minutes to 3 hours, and the second step may be performed by stirring at 10° C. to 35° C. at a rate of 1,000 rpm to 3,000 rpm for 6 hours to 24 hours, but the steps are not limited thereto.

For example, in a specific exemplary embodiment of the present invention, the first and second steps were performed by stirring at a rate of 1,700 rpm, which is the maximum speed of the magnetic stirrer in possession, but are not limited thereto.

A step of washing the nanogel comprising the polyamine-based polymer cross-linked by the oxamide bonds obtained from the second step with a $C_{1-4}$ alcohol may be further comprised. As the alcohol, ethanol may be used, but the alcohol is not limited thereto. Furthermore, after the washing, in order to recover the formed nanogel, a step of centrifuging at a rate of 7,000 rpm to 15,000 rpm may be further comprised. The washing step may be repeated several times, but is not limited thereto.

For example, the polymer solution may comprise the polyamine-based polymer at a concentration of 0.02 g/mL to 0.04 g/mL.

For example, the nonionic surfactant may be used at a weight ratio (w/w) of 1.5 times to 5 times relative to the mass of the polyamine-based polymer, and an oxalyl halide may be used at a volume ratio (v/w) of 0.3 times to 1 time relative to the mass of the polyamine-based polymer, respectively.

Further, the present invention may provide a contrast agent for ultrasound imaging, comprising the nanogel comprising the polyamine-based polymer cross-linked by oxamide bonds according to the present invention; a perfluorinated compound; and a nonionic polymeric surfactant.

For example, the perfluorinated compound is a compound which contains a large amount of fluorine, is in a liquid state at room temperature, and may be a chemical species having a gas-capturing ability, for example, high gas solubility. Non-limiting examples of the perfluorinated compound include perfluoropentane, perfluorohexane, perfluorooctylbromide, and perfluoro-15-crown-5-ether.

For example, the contrast agent of the present invention may be in the form of particles having a diameter of 30 nm to 1,000 nm.

The contrast agent of the present invention may react with hydrogen peroxide to generate carbon dioxide and expand by capturing the generated carbon dioxide therein to form microbubbles. The contrast agent of the present invention may expand into microbubbles having a diameter of 2 μm to 100 μm by capturing carbon dioxide, but is not limited thereto.

For example, the contrast agent of the present invention may further comprise a near-infrared fluorescent substance, and the presence of carbon dioxide can be detected from fluorescence of the near-infrared fluorescent substance. For example, the near-infrared fluorescent substance may be Cy5.5, but is not limited thereto, and similar fluorescent substances known in the art can be used without limitation. Meanwhile, the near-infrared fluorescent substance may be bound to the contrast agent by physical and/or chemical interactions. For example, the near-infrared fluorescent substance may be a molecule comprising a vinylsulfone group, a N-hydroxysuccinimidyl (NHS) group, or an isothiocyanate (ITC) group so that the near-infrared fluorescent substance can become attached to amine groups of the polyamine-based polymer by forming covalent bonds therewith, but is not limited thereto.

Furthermore, the present invention can provide a composition for ultrasound diagnosis of inflammatory diseases comprising the contrast agent for ultrasound imaging as an active ingredient. For example, the contrast agent in a solid state can be dispersed in an appropriate solvent such as physiological saline to be provided in an administrable form. For example, it may be administered by injecting directly or indirectly to a site where an inflammatory disease appears to have developed in an injection form, but is not limited thereto.

Inflammatory diseases that can be diagnosed by using the composition of the present invention are diseases whose main lesion is inflammation and refer to diseases which generate hydrogen peroxide in lesions, including, but not limited to, hepatitis; allergic diseases including allergic asthma, allergic rhinitis, allergic mucositis, hives, and anaphylaxis; myopathies including systemic sclerosis, dermatomyositis, and inclusion body myositis; arthritis; atopic dermatitis; psoriasis; asthma; multiple sclerosis; ssRNA and dsRNA viral infections; sepsis; multiple chondritis; scleroderma; eczema; gout; periodontal diseases; Behcet's disease; edema; angiitis; Kawasaki disease; diabetic retinitis; autoimmune pancreatitis; vasculitis; glomerulonephritis; acute and chronic bronchitis; and influenza infection. Furthermore, the inflammatory diseases may further include cancer diseases such as solid tumors and tumors that spread through blood, etc. occurring at head, neck, eyes, mouth, throat, esophagus, bronchus, larynx, pharynx, chest, bone, lung, colon, rectum, stomach, prostate, bladder, uterus, cervix, breast, ovary, testes, other reproductive organs, skin, thyroid, blood, lymph nodes, kidney, liver, pancreas, brain, and the central nervous system.

Further, the composition for ultrasound imaging of the present invention can be prepared through a step of ultrasonically dispersing an aqueous solution dissolving the nanogel comprising the polyamine-based polymer cross-linked by oxamide bonds; a perfluorinated compound; and a nonionic polymeric surfactant.

For example, the aqueous solution may comprise the nanogel, the perfluorinated compound, and the nonionic polymeric surfactant at a weight:volume:weight ratio of 1:(0.05 to 0.2):(1.5 to 3).

In particular, the aqueous solution may comprise the nanogel at a concentration of 0.05 g/mL to 0.2 g/mL.

Further, the aqueous solution may further comprise a near-infrared fluorescent substance, but is not limited thereto.

In particular, the near-infrared fluorescent substance may be used at a weight ratio of 0.03 to 0.1 relative to the weight of the nanogel.

The sixth aspect of the present invention provides a method for providing information for diagnosis of inflammatory diseases, comprising a first step of taking an ultrasound image of a subject to which the composition for ultrasound diagnosis was administered; and a second step of reading the ultrasound image to make a judgment that an inflammatory disease has occurred at a site where an increased signal is detected as compared to other normal tissues.

As used herein, the term "subject" refers to all animals, including humans, in which the inflammatory disease or a disease caused by oxidation has developed or is likely to develop, including monkey, cow, horse, sheep, pig, chicken, turkey, quail, cat, dog, mouse, rat, rabbit, or guinea pig.

(3) Advantageous Effects

Since the nanogel comprising the polyamine-based polymer cross-linked by oxamide bonds of the present invention can generate $CO_2$ at a controlled rate by reacting with hydrogen peroxide, it can be prepared as nanoparticles with perfluorohexane having an excellent gas-capturing ability to be usefully applied as a contrast agent for ultrasound imaging, and the contrast agent for ultrasound imaging can be used for the diagnosis of inflammatory diseases including cancer diseases.

DETAILED DESCRIPTION OF THE INVENTION

Hereinbelow, the present invention will be described in detail with accompanying exemplary embodiments. However, the exemplary embodiments disclosed herein are only for illustrative purposes and should not be construed as limiting the scope of the present invention.

Figure 1:
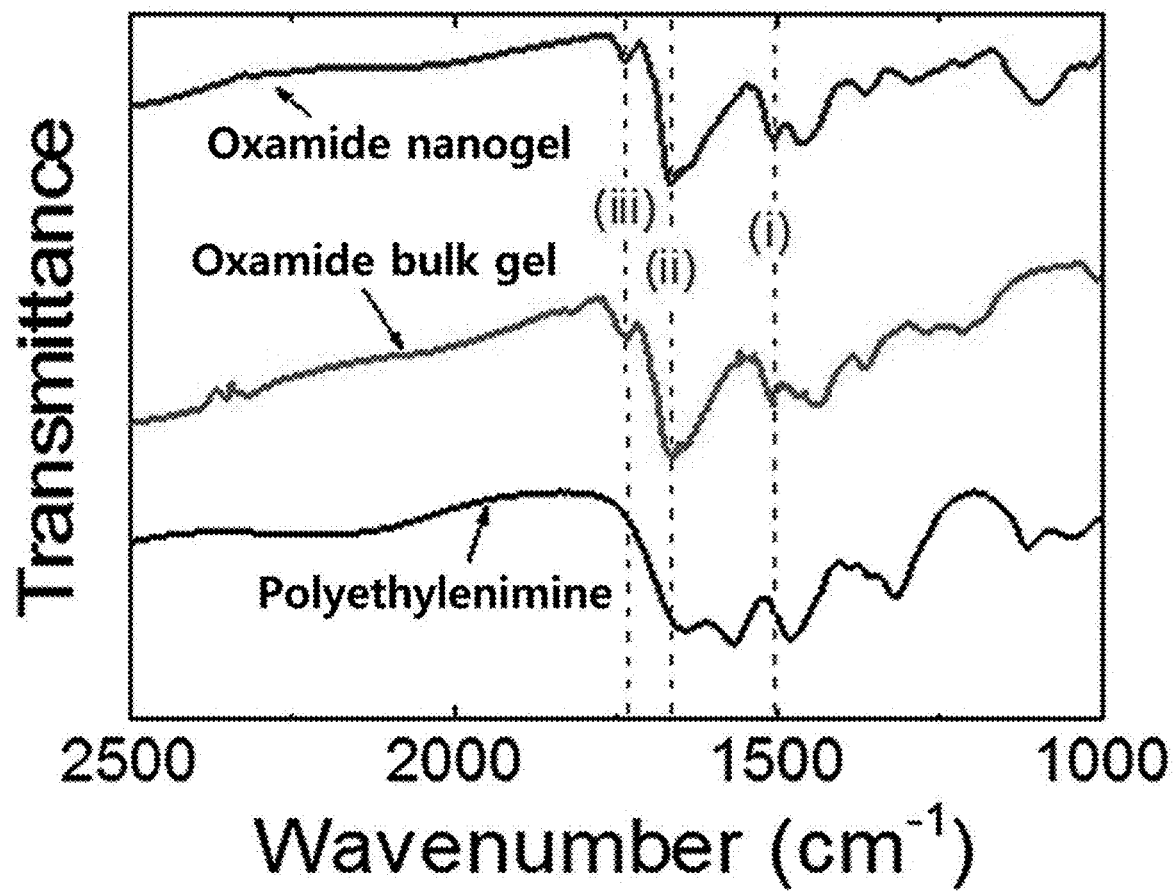
FIG. 1 shows an infrared spectroscopic spectrum of an oxamide nanogel according to an exemplary embodiment of the present invention.

Example 1: Preparation of Oxamide Nanogel Mediated by Reverse Micelle Method After 1.4 g of branched polyethylenimine (bPEI, molecular weight 600, Sigma-Aldrich, USA) was dissolved in 1 g of liquid nonionic surfactant tween 80 (Sigma-Aldrich, USA), it was mixed with 15 mL of cyclohexane (Daejung Chemicals & Metals Co., Ltd., Korea). A homogeneous reverse micelle dispersion was prepared by stirring the mixture at room temperature for 1 hour at a high speed. 0.2 mL of oxalyl chloride was added to the reverse micelle dispersion, and the formation of an oxamide nanogel was induced by further stirring at room temperature for 12 hours. By washing with ethanol (Daejung Chemicals & Metals Co., Ltd., Korea), residual organic matter and the organic solvent were removed from the oxamide nanogel dispersed in a reverse micelle state. Specifically, the oxamide nanogel dispersion in the reverse micelle state was poured into excess ethanol to remove tween 80 on the surface of the oxamide nanogel, and at the same time, the oxamide nanogel was induced to be selectively precipitated. The precipitated oxamide nanogel was collected, redispersed in excess ethanol, and centrifuged at a rate of 10,000 rpm for 1 hour to precipitate the oxamide nanogel. The redispersion and washing process by precipitation using ethanol were performed by repeating three times. The purified oxamide nanogel was vacuum dried at room temperature. In order to confirm the oxamide bonds comprised in the oxamide nanogel, the chemical structure of the formed oxamide nanogel was analyzed by measuring the infrared spectrum, and the results are shown in FIG. 1.

Figure 2A:
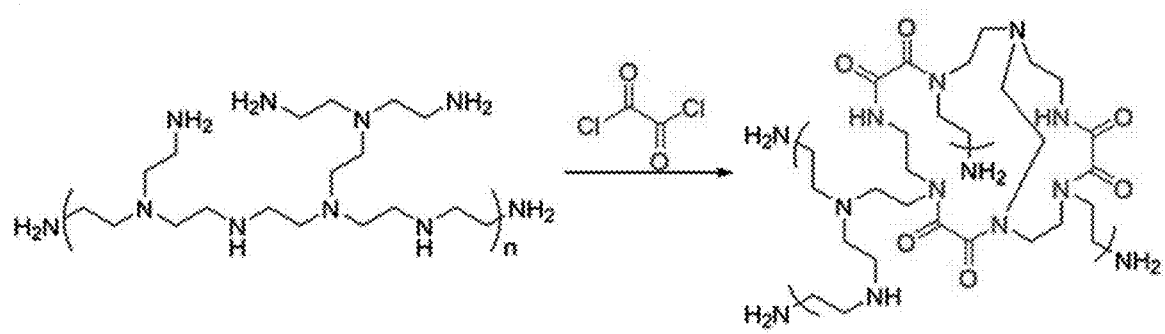
FIG. 2a shows diagrams of a synthesis method of an oxamide bulk gel by gelation reaction of polyethylenimine (PEI) and FIG. 2b shows optical images of PEI before and after the gelation reaction, as a comparison example of the present invention.

Comparative Example 1: Preparation of Oxamide Bulk Gel Using Gelation Reaction of Polyethylenimine After dissolving bPEI in dichloromethane (Daejung Chemicals & Metals Co., Ltd., Korea) at a concentration of 50 weight %, oxalyl chloride was added at 50 weight % relative to the bPEI. Thereafter, by stirring at room temperature for 1 minute at a high speed, an oxamide bulk gel was prepared by inducing the gelation reaction shown in FIG. 2a.

Figure 2B:
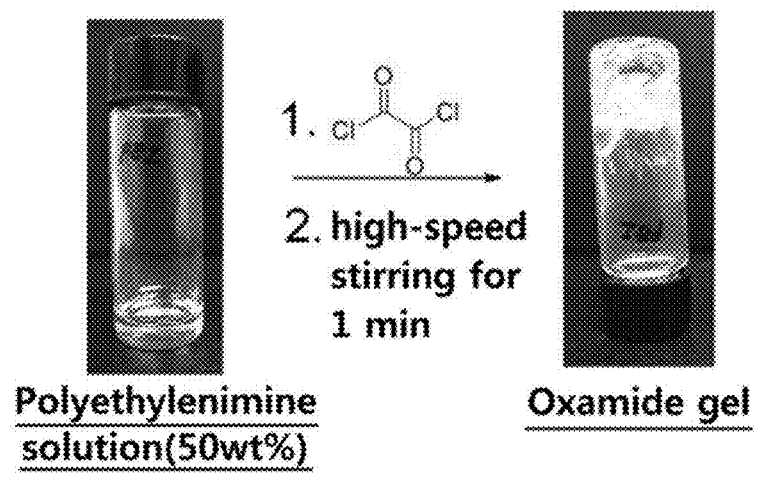

In order to confirm whether the oxamide bulk gel was formed, phase change during the gelation reaction of bPEI was observed (FIG. 2b). Further, the formation of oxamide bonds was confirmed by infrared spectroscopy, the chemical structure of the oxamide bulk gel was analyzed, and the recorded infrared spectrum was shown in FIG. 1.

Example 2: Preparation of Nano-Contrast Agent for Ultrasound Imaging Comprising Oxamide Nanogel After adding 10 mg of the oxamide nanogel prepared according to Example 1 to 1 mL of an aqueous solution in which Cy5.5 (0.5 mg, Bioacts, Korea), which is a near-infrared fluorescent substance comprising a vinylsulfone group, perfluorohexane (1 μL, Sigma-Aldrich, USA), which is a chemical species having gas-capturing ability, and Pluronic F-68 (20 mg, Sigma-Aldrich, USA), which is a polymeric surfactant, were mixed and dissolved, a nano-contrast agent containing the oxamide nanogel provided with near-infrared fluorescence and gas-capturing properties was prepared by ultrasonic dispersion. The prepared oxamide nano-contrast agent was centrifuged and redispersed in 1 mL of physiological saline (pH 7.4) to remove unbound Cy5.5. The nano-contrast agent for ultrasound imaging comprising the oxamide nanogel finally obtained by washing as described above was refrigerated and stored at 0° C. to 5° C.

Figure 3:
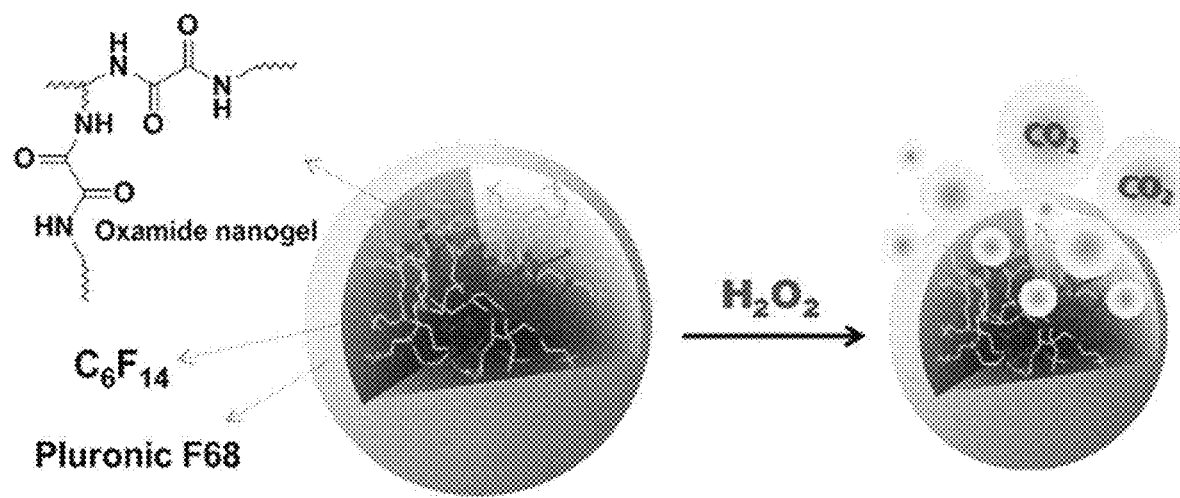
FIG. 3 schematically shows the structure and operation principle of the oxamide nanogel according to an exemplary embodiment of the present invention.
Figure 4:
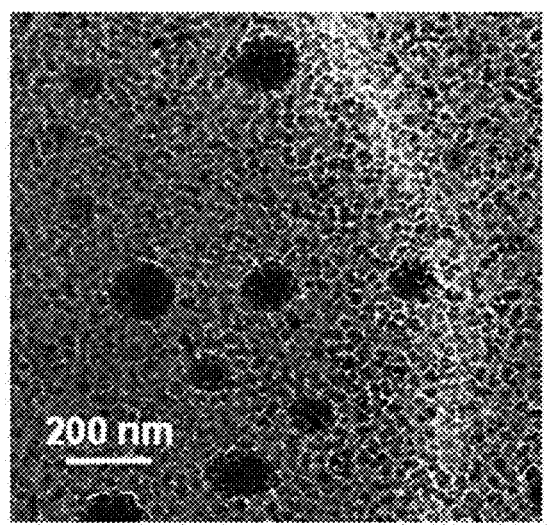
FIG. 4 is a transmission electron microscope (TEM) image of a nano-contrast agent comprising the oxamide nanogel, and a graph showing the size distribution thereof in a hydrated state calculated therefrom, according to an exemplary embodiment of the present invention.
Figure 4:
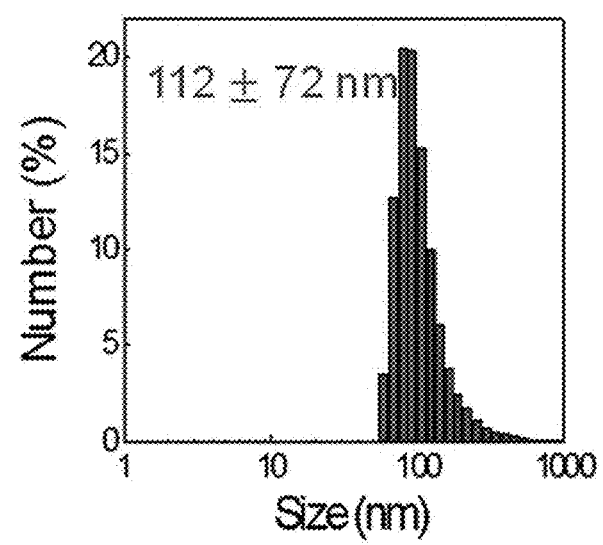
Figure 5A:
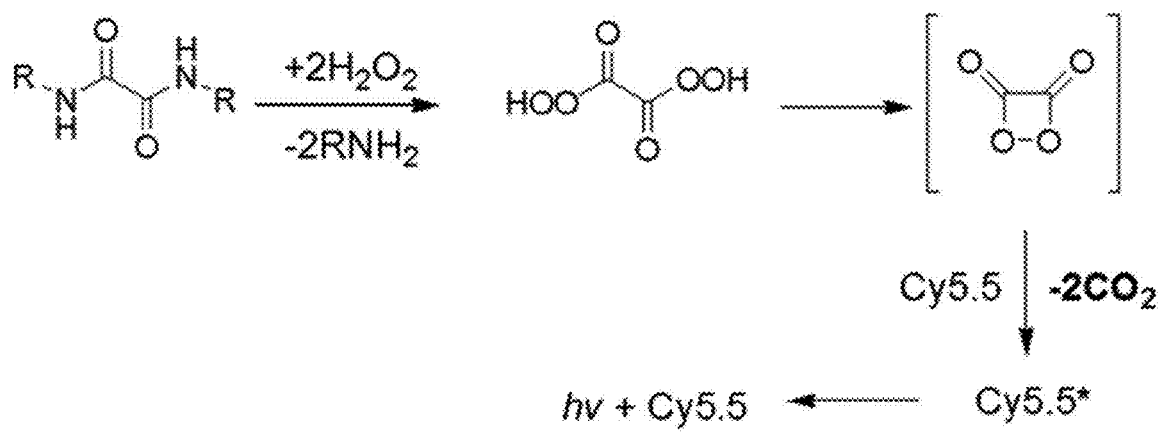
FIG. 5a shows the reaction mechanism of hydrogen peroxide-sensitive $CO_2$ generation and chemiluminescence of an oxamide group.
Figure 5B:
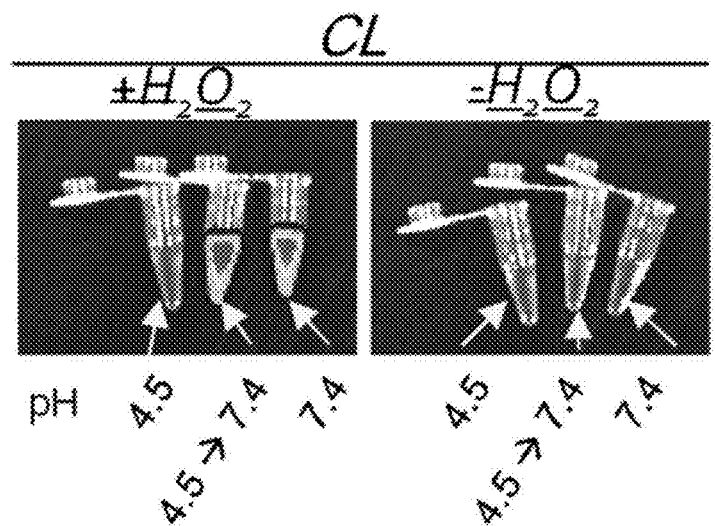
FIG. 5b shows images of hydrogen peroxide-sensitive chemiluminescence of the nano-contrast agent loading the oxamide nanogel.

A schematic design diagram of the nano-contrast agent for ultrasound imaging comprising the oxamide nanogel prepared as described above is shown in FIG. 3. The structure and shape of the prepared nano-contrast agent were analyzed using a transmission electron microscope and the dynamic light scattering method, and the results are shown in FIG. 4. In order to confirm that the oxamide bonds comprised in the nano-contrast agent were effectively dissociated to generate $CO_2$, which was sensitive to hydrogen peroxide, generated near-infrared fluorescence of Cy5.5, which was mediated by the chemiluminescence mechanism of the oxamide group shown in FIG. 5a, was observed, and the results are shown in FIG. 5b. Substantially, in the case of oxalate bonds, their reactivity with hydrogen peroxide is high so that under exposure to hydrogen peroxide, oxalate bonds are rapidly broken to exhibit chemiluminescence phenomena, but the dissociation of oxamide bonds by hydrogen peroxide as shown in FIG. 5a is low in reactivity, and therefore it may be difficult to observe chemiluminescence phenomena when exposed to hydrogen peroxide. However, in the case of the present invention, since the oxamide bonds of the nanogel are included in the polyethylenimine network including many amine groups so that the amine groups contained therein can provide a basic environment, the dissociation reaction of the oxamide bonds by hydrogen peroxide can be promoted by a base-catalyzed effect therefrom. Therefore, whereas chemiluminescence phenomena due to the dissociation of the oxamide bonds by hydrogen peroxide were observed at neutral pH due to the base-catalyzed mechanism mediated by amine groups, chemiluminescence due to the dissociation of the oxamide bonds by hydrogen peroxide was not observed under acidic pH because the base-catalyzed effect was excluded. This can be confirmed in the left drawing of FIG. 5b.

Figure 6A:
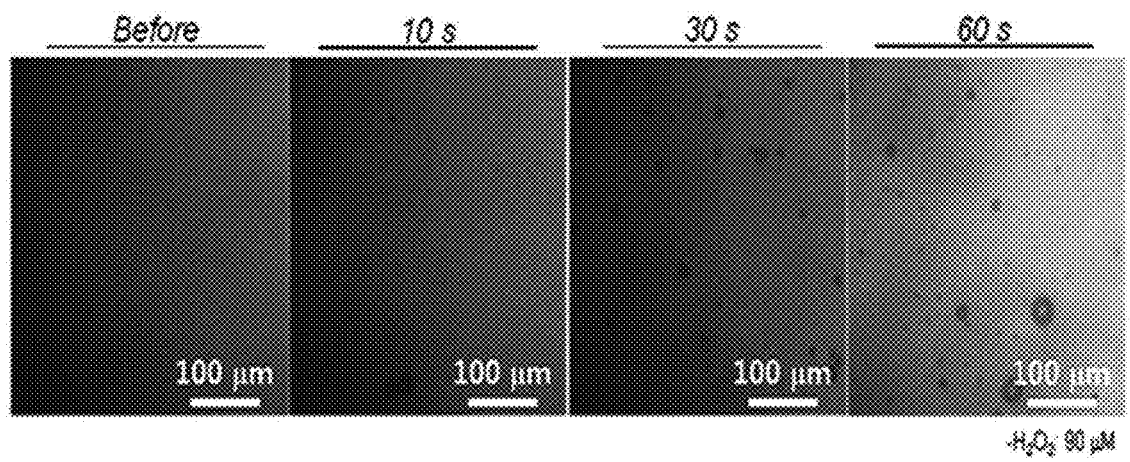
FIG. 6a shows hydrogen peroxide-sensitive bubble formation of the oxamide nanogel illustrated in images observed with an optical microscope and FIG. 6b shows images observed with a cryo-scanning electron microscope (cryo-SEM)
Figure 6B:
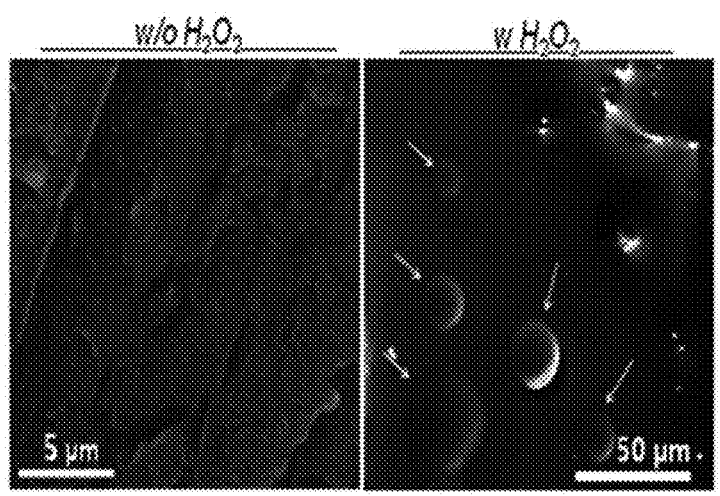
Figure 6C:
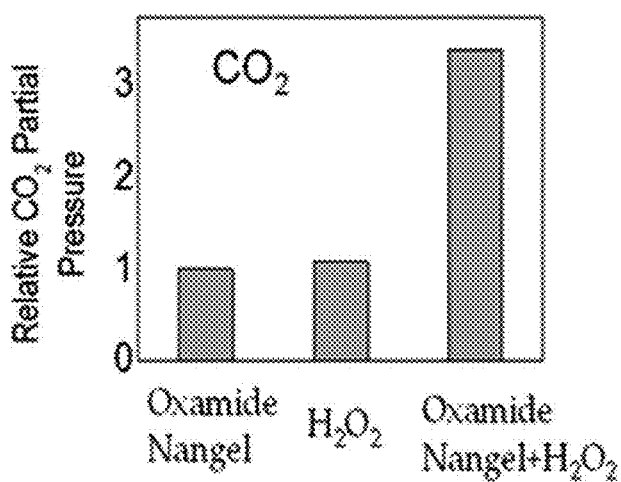
FIG. 6c shows the results confirming $CO_2$ formation by mass spectrometry, according to an exemplary embodiment of the present invention.

Example 3: Evaluation of Microbubble-Forming Ability of Nano-Contrast Agent Comprising Oxamide Nanogel and Ultrasonic Signal Detection Using the Same 3-1. Microbubble-Forming Ability of Nano-Contrast Agent Comprising Oxamide Nanogel by Hydrogen Peroxide Sensitivity In order to confirm whether the nano-contrast agent comprising the oxamide nanogel formed microbubbles due to the dissociation of the oxamide bonds sensitive to hydrogen peroxide, after hydrogen peroxide was added to the aqueous dispersion of the nano-contrast agent prepared according to Example 2 to a final concentration of 90 μM, the microbubble formation was observed with an optical microscope in real time, and the results are shown in FIG. 6a. Further, immediately after hydrogen peroxide was added to the aqueous dispersion of the nano-contrast agent at the same concentration as above, microbubbles generated were frozen by immersing in liquid nitrogen and observed with a cryo-scanning electron microscope (cryo-SEM), and the results are shown in FIG. 6b. Furthermore, in order to confirm that the generated microbubbles contained $CO_2$, after applying 2 to 3 drops of a 30% aqueous hydrogen peroxide solution to 400 mg of the oxamide nanogel in a dry state, the partial pressure of $CO_2$ was measured using a mass spectrometer (HPR20, Hiden Analytical, UK), and the results are shown in FIG. 6c.

Figure 7A:
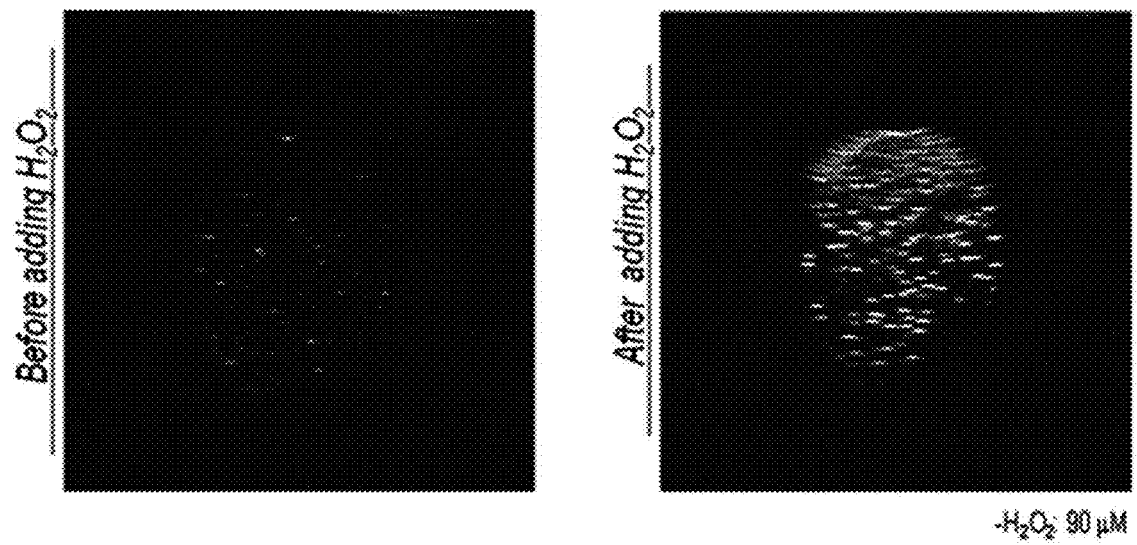
FIG. 7a shows images of ultrasound imaging processing experiments and FIG. 7b shows a graph illustrating the intensity of ultrasound signals detected therefrom, using the oxamide nanogel according to an exemplary embodiment of the present invention.
Figure 7B:
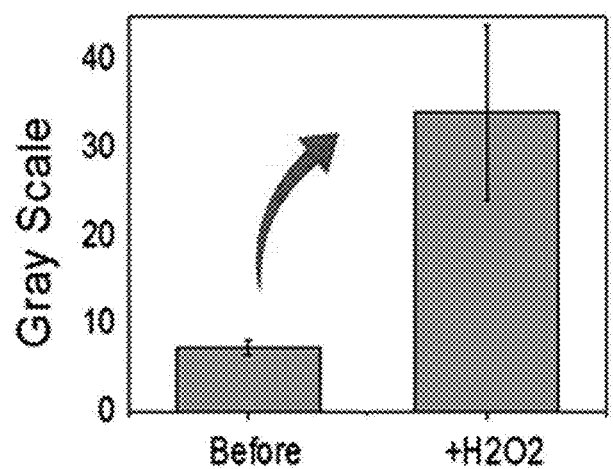

3-2. Detection of Ultrasonic Signals Mediated by Nano-Contrast Agent Comprising Oxamide Nanogel by Hydrogen Peroxide Sensitivity In order to observe ultrasonic signals by the nano-contrast agent prepared according to Example 2, after dissolving agar in water at a concentration of 3 weight %, an agar-gel mold was prepared by cooling at room temperature, and an empty space in a cylindrical form having a volume of 500 μL was formed on side surface of the mold. After adding 300 μL of the nano-contrast agent in the formed empty space, hydrogen peroxide was added to a final concentration of 90 μM, ultrasound imaging was performed at a frequency of 40 MHz using an ultrasound imaging device (Vevo770, High-Resolution Micro-Imaging System; Visual sonics, Canada), and the results are shown in FIGS. 7a and 7b. FIG. 7a shows ultrasound images, and FIG. 7b shows quantitative signal intensity extracted therefrom. As shown in FIGS. 7a and 7b, the ultrasonic signals before and after the addition of hydrogen peroxide showed a significant difference that could easily be distinguished by the naked eye, and it was confirmed from a numerical view that the signals were increased by about 5 times.

Figure 8A:
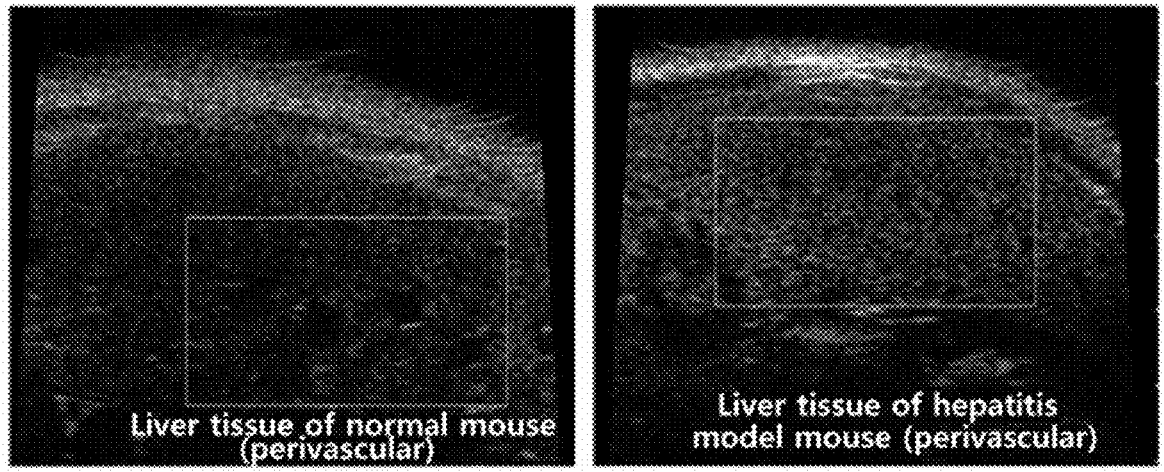
FIG. 8a shows ultrasound images of a relevant tissue and/or a graph illustrating signal intensity of a hepatitis model mouse and FIG. 8b shows images of a cancer model mouse, under administration of the oxamide nanogel according to an exemplary embodiment of the present invention.

Example 4: Evaluation of Microbubble-Forming Ability of Nano-Contrast Agent Comprising Oxamide Nanogel in Inflammatory Disease Model and Ultrasonic Signal Detection Using the Same 4-1. Ultrasound Imaging of Hepatitis Mouse Model Administered with Oxamide Nanogel 100 μL of physiological saline in which 1 mg of *P. acnes* was dispersed was intravenously injected to five-week-old male mice (Orient Bio Inc., Korea), and after 7 days, 200 μL of physiological saline containing 1 μg of lipopolysaccharide (LPS) was further intravenously injected to prepare hepatitis mouse models. The hepatitis-induced mouse was fixed on a pad of the ultrasound imaging device, and 200 μL of the nano-contrast agent comprising the oxamide nanogel prepared according to Example 2 was directly injected to the liver tissue with a catheter syringe. Ultrasound imaging was performed before and after the nano-contrast agent was applied, and the results are shown in FIG. 8a. As shown in FIG. 8a, it was confirmed that normal tissues and the hepatitis-induced liver tissue could be distinguished by the naked eye through ultrasound imaging. This indicates that the nano-contrast agent comprising the oxamide nanogel according to the present invention can be valuably used as a contrast agent in the ultrasound diagnosis of inflammatory diseases.

Figure 8B:
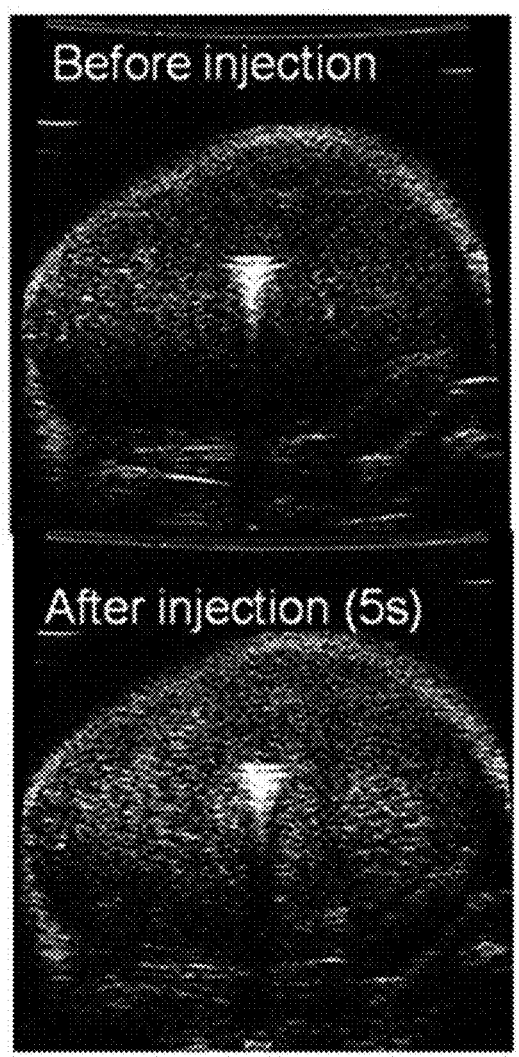
Figure 8B:
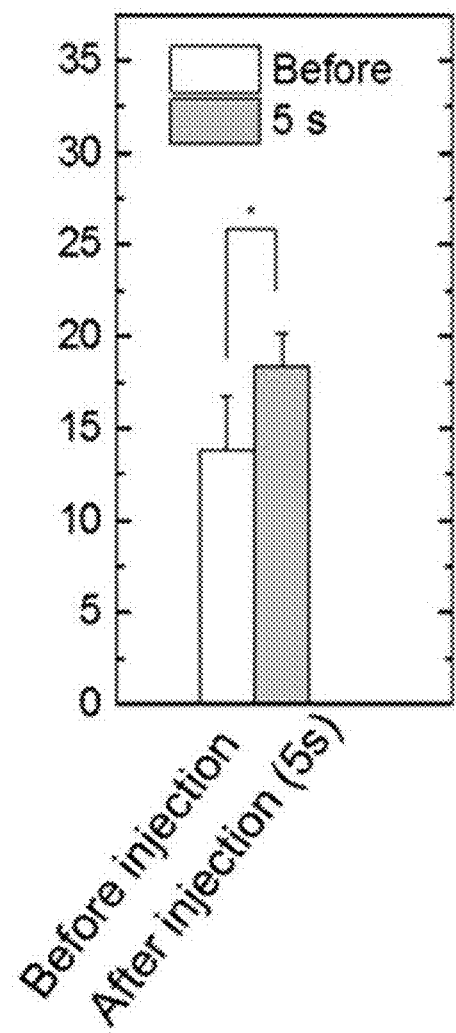

4-2. Ultrasound Imaging of Cancer Mouse Model Administered with Oxamide Nanogel $1 \times 10^6$ SCC7 cells were hypodermically injected into the left thigh region of 5-week-old male mice (Orient Bio Inc., Korea) to prepare cancer mouse models. At 10 to 15 days after transplanting the cancer cells, it was confirmed that solid cancer was formed, and 50 μL of the nano-contrast agent comprising the oxamide nanogel prepared according to Example 2 was directly injected into the formed cancer tissue. Ultrasound imaging was performed before and after the nano-contrast agent was applied, and the results are shown in FIG. 8b. As shown in FIG. 8b, it was confirmed that the ultrasound imaging signals after the injection were increased by about 40% compared to the ultrasound imaging signals before the injection and such difference could be confirmed from the images by the naked eye. This indicates that the nano-contrast agent comprising the oxamide nanogel according to the present invention can be used for ultrasound diagnosis of cancer diseases.

What is claimed is:

1. A contrast agent for ultrasound imaging, comprising a nanogel comprising a polyamine-based polymer cross-linked by oxamide bonds; a perfluorinated compound; and a nonionic polymeric surfactant,
    wherein the polyamine-based polymer is a linear or branched poly(C1-4 alkylene)imine,
    wherein the oxamide bonds are formed at a ratio of 10 mol % to 50 mol % relative to the total number of amine groups,
    wherein the amine groups, which are not involved in formation of the oxamide bonds, have a ratio of 50 mol % to 90 mol % relative to the total number of amine groups and catalyze dissociation reaction of the oxamide bonds, and
    wherein the contrast agent comprises the nanogel, the perfluorinated compound, and the nonionic polymeric surfactant at a weight:volume:weight ratio of 1:(0.05 to 0.2):(1.5 to 3).

2. The contrast agent of claim 1, wherein the contrast agent is in the form of a particle having a diameter of 30 nm to 1,000 nm.

3. The contrast agent of claim 1, wherein the contrast agent reacts with hydrogen peroxide to generate carbon dioxide and expands by capturing the generated carbon dioxide therein to form microbubbles.

4. The contrast agent of claim 1, further comprising a near-infrared fluorescent substance.

5. A composition for ultrasound imaging of inflammation, comprising the contrast agent for ultrasound imaging of claim 1 as an active ingredient.

6. A method for preparing a contrast agent for ultrasound imaging of claim 1, comprising ultrasonically dispersing an aqueous solution dissolving nanogel comprising a polyamine-based polymer cross-linked by oxamide bonds; a perfluorinated compound; and a nonionic polymeric surfactant,
    wherein the polyamine-based polymer is a linear or branched poly(C1-4 alkylene)imine,
    wherein the oxamide bonds are formed at a ration of 10 mol % to 50 mol % relative to the total number of amine groups,
    wherein the amine groups, which are not involved in formation of the oxamide bonds, have a ratio of 50 mol % to 90 mol % relative to the total number of amine groups and catalyze dissociation reaction of the oxamide bonds, and
    wherein the contrast agent comprises the nanogel, the perfluorinated compound, and the nonionic polymeric surfactant at a weight:volume:weight ratio of 1:(0.05 to 0.2):(1.5 to 3).

7. The method of claim 6, wherein the aqueous solution comprises the nanogel at a concentration of 0.05 g/mL to 0.2 g/mL.

8. The method of claim 6, wherein the aqueous solution further comprises a near-infrared fluorescent substance.

9. The method of claim 8, wherein the near-infrared fluorescent substance is comprised at a weight ratio of 0.03 to 0.1 relative to the weight of the nanogel.

* * * * *